(12) United States Patent
Copf, Jr.

(10) Patent No.: US 8,366,718 B2
(45) Date of Patent: Feb. 5, 2013

(54) PREPARATION DEVICE FOR PREPARING AN INTERVERTEBRAL DISC COMPARTMENT

(76) Inventor: Franz Copf, Jr., Stuttgart (DE)

( * ) Notice: Subject to any disclaimer, the term of this patent is extended or adjusted under 35 U.S.C. 154(b) by 984 days.

(21) Appl. No.: 11/994,789

(22) PCT Filed: Jul. 6, 2006

(86) PCT No.: PCT/EP2006/006610
§ 371 (c)(1),
(2), (4) Date: Apr. 22, 2008

(87) PCT Pub. No.: WO2007/003439
PCT Pub. Date: Jan. 11, 2007

(65) Prior Publication Data
US 2008/0200987 A1    Aug. 21, 2008

Related U.S. Application Data

(60) Provisional application No. 60/696,881, filed on Jul. 6, 2005.

(30) Foreign Application Priority Data

Feb. 10, 2006   (EP) .................................... 06002776

(51) Int. Cl.
*A61B 17/58* (2006.01)
*A61B 17/60* (2006.01)
*A61F 2/00* (2006.01)

(52) U.S. Cl. ........................ 606/99; 606/86 R; 606/86 A
(58) Field of Classification Search ................ 606/86 R, 606/87, 90, 99, 86 A
See application file for complete search history.

(56) References Cited

U.S. PATENT DOCUMENTS 5,944,658 A    8/1999   Koros et al.
(Continued)

FOREIGN PATENT DOCUMENTS

| EP | 296 872 | 12/1988 |
|----|---------|---------|
| EP | 955 021 | 11/1999 |
| WO | WO 2004/058098 | 7/2004 |

(Continued)

OTHER PUBLICATIONS

International Search Report and Written Opinion from corresponding International Application No. PCT/EP2006/006610 dated Jun. 22, 2006.

*Primary Examiner* — Thomas C. Barrett
*Assistant Examiner* — Christine Nelson
(74) *Attorney, Agent, or Firm* — Lempia Summerfield Katz LLC

(57) ABSTRACT

The invention relates to a preparation device for preparing an intervertebral disc compartment (14) which is delimited by a first and a second vertebra (16, 18). Such a preparation is carried out prior to the insertion of an intervertebral disc prosthesis (110), in order to guarantee a correct positioning of the intervertebral disc prosthesis between the vertebrae (16, 18). The preparation device (10) comprises a reference frame (22), which is capable of being fastened above an operating table (12), and a first fixing element (58) which is capable of being rigidly connected to the first vertebra (16) are capable of being fastened to the reference frame (22) in varying first positions. A second fixing element (68) is capable of being rigidly connected to the second vertebra (18) and capable of being fastened to the reference frame (22) in varying second positions. A material-abrading tool (78) is capable of being fastened to the reference frame (22), preferably in varying positions.

16 Claims, 10 Drawing Sheets

U.S. PATENT DOCUMENTS

| | | |
|---|---|---|
| 2002/0161446 A1 | 10/2002 | Bryan et al. |
| 2003/0014116 A1* | 1/2003 | Ralph et al. ............... 623/17.16 |
| 2004/0230191 A1 | 11/2004 | Frey et al. |
| 2005/0033291 A1 | 2/2005 | Ebara |
| 2005/0187627 A1 | 8/2005 | Ralph et al. |
| 2005/0203533 A1* | 9/2005 | Ferguson et al. ............... 606/90 |
| 2006/0015183 A1 | 1/2006 | Gilbert et al. |

FOREIGN PATENT DOCUMENTS

| | | |
|---|---|---|
| WO | WO 2005/044151 | 5/2005 |
| WO | WO 2005/074850 | 8/2005 |
| WO | WO2005/104996 | 11/2005 |
| WO | WO2006/004848 | 1/2006 |
| WO | WO 2006/042486 | 4/2006 |

* cited by examiner

PREPARATION DEVICE FOR PREPARING AN INTERVERTEBRAL DISC COMPARTMENT

CROSS-REFERENCE TO RELATED APPLICATIONS

This U.S. national phase application is based on international applications no. PCT/EP2006/006610, filed on Jul. 6, 2006, and claims priority benefit of U.S. provisional application Ser. No. 60/696,881 filed Jul. 6, 2005 and claims priority to European patent application EP 06002766.0 filed Feb. 10, 2006. The full disclosure of these earlier applications is incorporated herein by reference.

BACKGROUND OF THE INVENTION

1. Field of the Invention

The invention relates to a preparation device for preparing an intervertebral disc compartment which is delimited by a first and a second vertebra. Such a preparation is carried out prior to the insertion of an intervertebral disc prosthesis, in order to ensure a correct positioning of the intervertebral disc prosthesis between the vertebrae.

2. Description of the Prior Art

US 2002/0161446 A1 discloses a material-abrading tool which is capable of being fastened to a reference frame in various angular positions relative to the vertical. Prior go the preparation of the intervertebral disc compartment, a radiograph of the segment of the vertebral column in question is taken from the side. On the basis of this radiograph, the setting angle of the tool on the reference frame with respect to the vertical is determined. Then the reference frame is fastened laterally to the operating table, so that it extends over and beyond the patient. Via a ventral access canal the cervical vertebrae in question are exposed, the intervertebral disc that is present is removed, and the wedge-shaped tool is introduced into the exposed intervertebral disc compartment at the setting angle determined in advance. With the aid of the tool the vertebrae delimiting the intervertebral disc compartment are machined in such a manner that plane abutment faces arise for the intervertebral disc prosthesis.

However, it has become evident that in the course of intervertebral disc operations that are carried out using such known preparation devices complaints occur relatively frequently, the cause of which is to be found in incorrect loadings of the segment of the vertebral column in question.

SUMMARY OF THE INVENTION

For this reason, an object of the invention is to specify a preparation device with which the risk of later complaints of such a type is reduced.

This object is achieved by means of a preparation device for preparing an intervertebral disc compartment, which is delimited by a first and a second vertebra, for the insertion of an intervertebral disc prosthesis, with:
a) a reference frame which is capable of being fastened above an operating table;
b) a first fixing element which is capable of being rigidly connected to the first vertebra and capable of being fastened to the reference frame in varying first positions;
c) a second fixing element which is capable of being rigidly connected to the second vertebra and capable of being fastened to the reference frame in varying second positions;
d) optionally a material-abrading tool which is capable of being fastened to the reference frame in varying positions.

The invention is based on the perception that an intervertebral disc prosthesis can only alleviate complaints with respect to the vertebral column efficaciously, or eliminate them completely, when the anatomical specifications of the segment of the vertebral column in question are taken into account as far as possible. These include, in particular, the consideration that the intervertebral disc prosthesis is positioned in such a manner that the center of motion, which is predetermined by the vertebrae adjoining the intervertebral disc compartment, is retained as far as possible. The center of motion corresponds to the swivel axis or swivel point about which the two vertebrae are able to swivel relative to one another. More particularly, the center of motion is determined by the ventral intervertebral disc system and also by two dorsal joint parts of the spinal canal.

The muscular and ligamentous apparatus surrounding the segment of the vertebral column in question is matched to the center of motion.

However, if an intervertebral disc prosthesis, the joint of which is not optimally matched to the anatomically predetermined center of motion, is inserted into the intervertebral disc compartment, this muscular and ligamentous apparatus is loaded unnecessarily, which generally gives rise to complaints in the patient.

In the case of the device known from US 2002/0161446 A1 which was mentioned at the outset it is not possible to obtain the anatomically predetermined center of motion by means of the implanted intervertebral disc prosthesis. This is related, on the one hand, to the fact that the radiograph taken pre-operatively, on the basis of which the setting angle for the tool is determined, registers the segment of the vertebral column in the form that it takes in the affected patient. In this state, however, the vertebrae may have been displaced by reason of highly diverse causes—for example, osseous hypertrophies or intervertebral disc deformations—in such a way that the position of the vertebrae differs considerably from that of a healthy vertebral column. If the setting angle of the tool is determined on the basis of such a radiograph, the intervertebral disc prosthesis is ultimately implanted in such a way that it merely replaces a part of the affected vertebral column, but without transferring the latter back into a healthy position.

On the other hand, particularly in the course of operations in the cervical vertebral segment of the vertebral column, it frequently happens that the relatively small cervical vertebrae are displaced in the course of the exposure of the ventral access canal. These displacements are not taken into account in the course of the removal of material by the tool and the subsequent implanting of the intervertebral disc prosthesis, since the establishment of the setting angle is undertaken solely on the basis of the radiograph taken pre-operatively.

With the aid of the alignable fixing elements according to the invention, on the other hand, it is possible firstly to transfer the vertebrae delimiting the intervertebral disc compartment into a position such as corresponds to the healthy segment of the vertebral column of the patient being operated on in the given case.

For the purpose of determining this position, various methods may be employed.

If still older radiographs of the as yet unaffected vertebral column of the patients are available, the position of the vertebrae can be determined on the basis of these radiographs. In addition, there is the possibility of inferring from the position of the adjacent vertebrae the position of the vertebrae delimiting the intervertebral disc compartment such as could be observed in the case of a healthy vertebral column. A further possibility consists in distracting the vertebrae during the operation with the aid of the fixing elements. Provided that the surrounding ligamentous apparatus has been preserved, the vertebrae place themselves in a position such as might be observed in the case of a healthy vertebral column.

Conventional intervertebral disc prostheses consist of two supporting plates which each bear a part of a ball-and-socket joint. The supporting plates have flat external surfaces by which they are supported on flat-milled abutment faces of the vertebrae. The position of the abutment faces consequently determines the position of the intervertebral disc prosthesis between the two vertebrae. A part of the ball-and-socket joint is exchangeably fastened to the supporting plate, in order to take account of varying spacings between the vertebrae.

However, with such known intervertebral disc prostheses the center of motion can be obtained reliably only when one is prepared to abrade relatively large amounts of the healthy vertebral material. In order to avoid this, the use is recommended of intervertebral disc prostheses in which both parts of the ball-and-socket joint are exchangeable. This allows the spacing of the spherical ball surfaces from the abutment faces to be adapted to the height of the intervertebral disc compartment and to the position of the center of motion. Intervertebral disc prostheses of such a type are described in the international patent application entitled "Intervertebral disc prosthesis" filed on the same day by the applicant. The full content of this other application is hereby incorporated by reference.

A further advantage with the use of the fixing elements consists in the fact that the forces required for the alignment are supplied externally, and not via adjacent vertebrae. In addition, an alignment extracorporeally is possible with the aid of fixing elements that have been introduced percutaneously, even when a dorsal or ventral access canal for the intervertebral disc prosthesis is to be created only at a later time.

BRIEF DESCRIPTION OF THE DRAWINGS

Various features and advantages of the present invention may be more readily understood with reference to the following detailed description taken in conjunction with the accompanying drawing in which.

DESCRIPTION OF PREFERRED EMBODIMENTS

Figure 1:
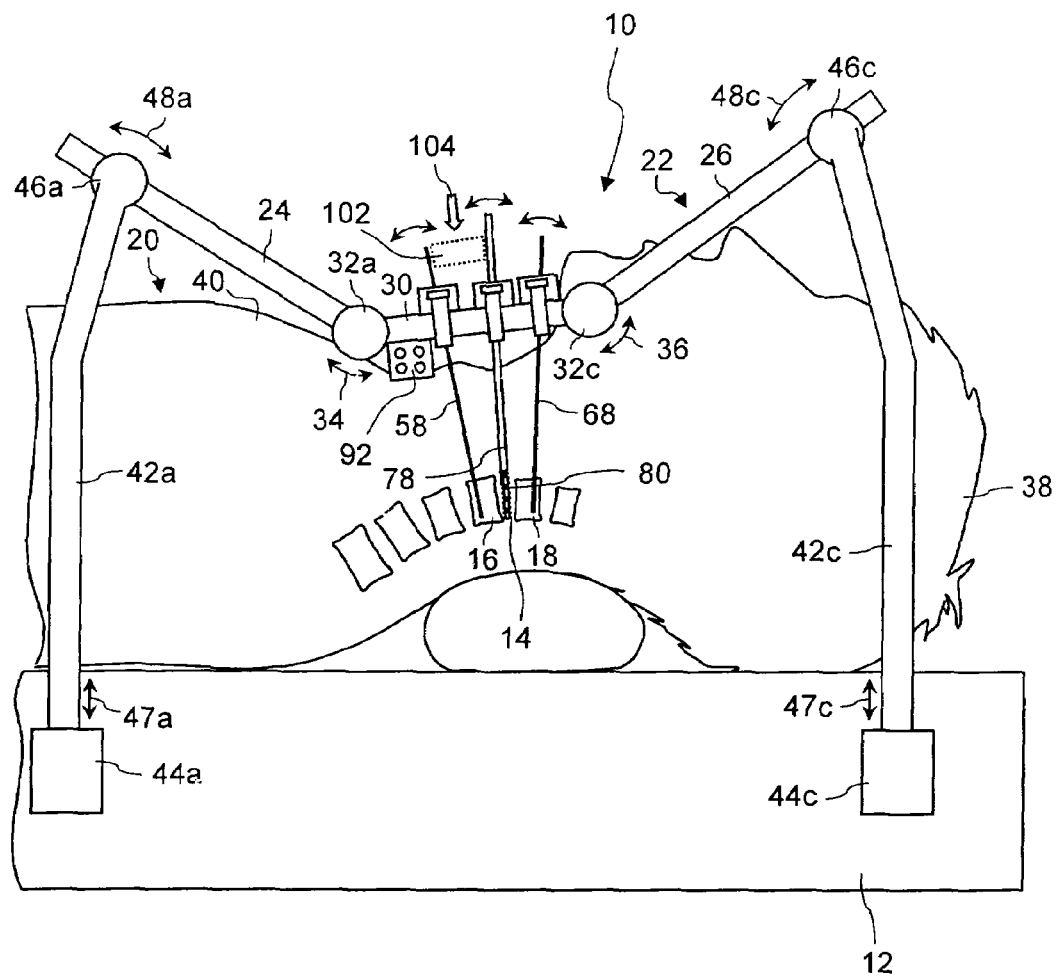
FIG. 1 is a schematic side view of a preparation device according to the invention.
Figure 2:
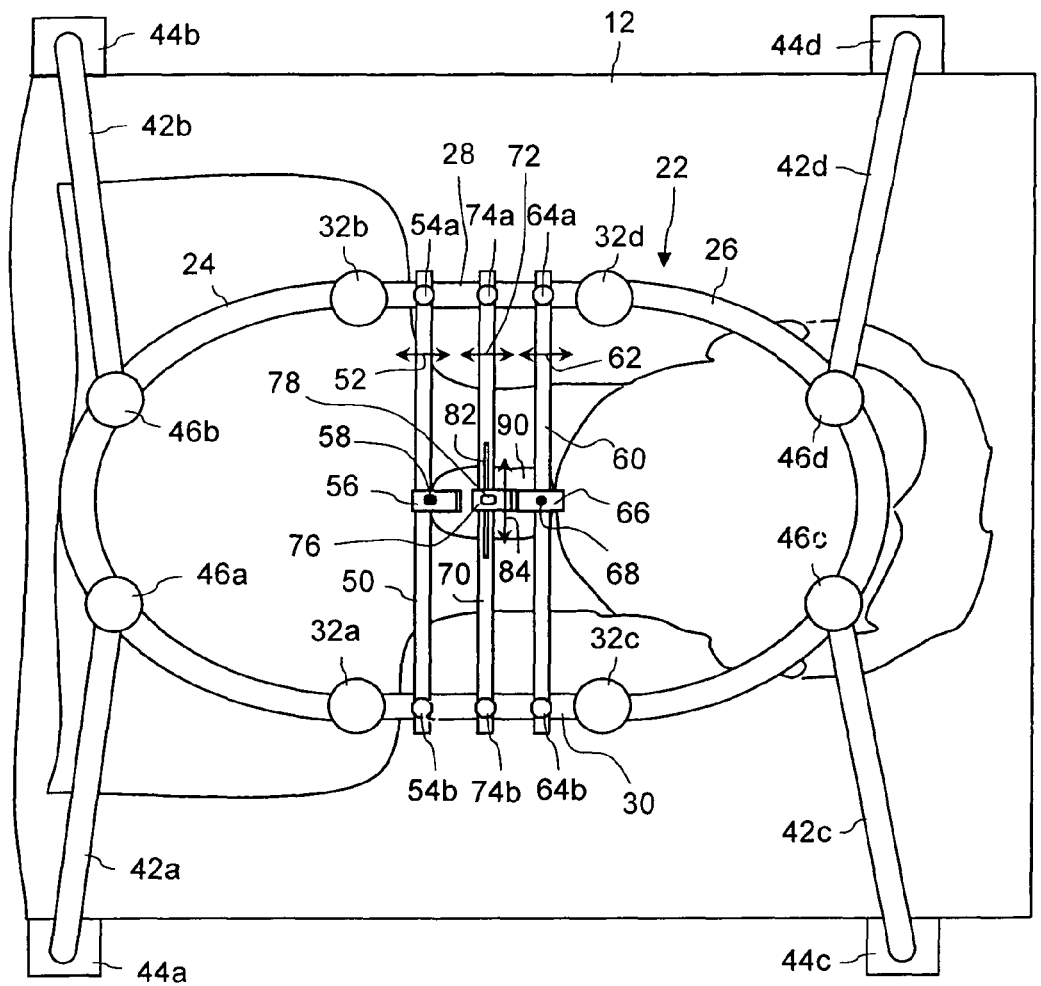
FIG. 2 is a top view of the preparation device shown in FIG. 1.

FIGS. 1 and 2 show a preparation device according to the invention in a greatly schematised side view and top view, respectively. The preparation device is denoted in its entirety by 10 and is fastened to an operating table 12. The device 10 serves for preparing an intervertebral disc compartment 14, which is formed between a first vertebra 16 and a second vertebra 18 of a patient 20, for the insertion of an intervertebral disc prosthesis. In the embodiment that is represented in FIGS. 1 and 2, the vertebrae 16, 18 are cervical vertebrae which are shown, for the sake of simplicity, without dorsal vertebral processes.

The preparation device 10 has the task of moving the vertebrae 16, 18 into an anatomically correct position before the prosthesis is inserted. The anatomically correct position is the position that the vertebrae 16, 18 would have if the patient's vertebral column was still healthy. Before or after the vertebrae have been brought into their anatomically correct position, the intervertebral disc compartment 14 can be machined with the aid of a material-abrading tool in such a way that the intervertebral disc prosthesis can be inserted into the intervertebral disc compartment in optimal position.

The preparation device 10 has a reference frame 22 which is constructed above the patient 20 who lies on his/her back on the operating table 12. The reference frame 22 has two arcuate brackets 24, 26 each having a circular cross-section. The two brackets 24, 26 are connected to one another via rails 28, 30, that also have a circular cross-section. This connection is made via joint elements 32a, 32b, 32c, 32d, which in FIGS. 1 and 2 are represented in schematised manner fixable as ball-and-socket joints. As can best be discerned in FIG. 1, the joint elements 32a, 32b, 32c, 32d allow the brackets 24, 26 to be swivelled relative to the rails 28, 30. In FIG. 1 the swivelling capability is indicated by arrows 34, 36.

The brackets 24, 26 are so wide that in the angled position shown in FIG. 1 they extend over the head 38 and the chest 40 of the patient 20. The rails 28, 30 can thus be lowered very close to the neck of the patient 20 without appreciably restricting the access canal to the cervical region for the surgeon.

The brackets 24, 26 are engaged by first supports 42a, 42b and second supports 42c, 42d, respectively, which align the reference frame 22 in relation to the operating table 12. For this purpose, the supports 42a, 42b, 42c, 42d are received in height-adjustable manner in sockets 44a, 44b and 44c, 44d, respectively, which are firmly connected to the operating table 12. The displaceability of the supports 42a, 42b in the vertical direction is indicated in FIG. 1 by arrows 47a, 47b.

The supports 42a, 42b and 42c, 42d are fastened to the brackets 24, 26, respectively, via second joint elements 46a, 46b and 46c, 46d, respectively. The second joint elements 46a, 46b, 46c, 46d are designed in such a manner that the brackets 24, 26 can be fixed in varying angular positions. The swivelling capability of the brackets 24, 26 relative to the supports 42a, 42b, 42c, 42d is indicated in FIG. 1 by arrows 48a, 48c.

Furthermore, the second joint elements 46a, 46b, 46c, 46d enable the entire reference frame 22 to be tilted about a longitudinal axis that extends parallel to the longitudinal direction of the operating table 12. The tiltability is assisted by the fact that the second joint elements 46a, 46b, 46c, 46d enclose the tubular brackets 24, 26, so that the brackets 24, 26 in the second joint elements 46a, 46b, 46c, 46d can be pushed back and forth also in the aforementioned longitudinal direction. Such a tilting can be generated, for example, by the supports 42a, 42c situated on one side of the operating table 12 being drawn out of, or pushed further into, the sockets 44a and 44c, respectively. In case sockets 44a, 44b, 44c, 44d which are already available on the operating table do not enable adjustability in height, the supports 42a, 42b, 42c, 42d as such may also be of length-adjustable design, for example with the aid of a threaded pinion.

With its ends a first slide 50 encompasses the rails 28, in such a manner that it is capable of being moved on the rails 28, 30 in the longitudinal direction indicated by an arrow 52 and capable of being locked at arbitrary longitudinal positions with the aid of locking screws 54a, 54b or similar fixing means. The first slide 50 bears a first clamping element 56 which is firmly connected to the first slide 50 but which may also be capable of being fixed in varying positions along the longitudinal direction of the first slide 50. The first clamping element 56 has the task of being able to fix a first fixing screw 58 in varying angular positions within a swivel plane that is perpendicular to a reference plane defined by the rails 28, 30 and that extends parallel to the rails 28, 30. For this purpose the clamping element 56 may include, for example, a cylinder, which is supported so as to be capable of swivelling, with a bore into which the first fixing screw 58 can be introduced and fixed.

A second slide 60 is likewise capable of being moved in longitudinally displaceable manner on the slides 28, 30 in a direction indicated by an arrow 62 and capable of being fixed on the rails 28, 30 in an arbitrary longitudinal position with the aid of locking screws 64a, 64b. The second slide 60 bears a second clamping element 66 which is constructed so as to be analogous to the first clamping element 56 and which serves for fixing a second fixing screw 68.

Between the two slides 50, 60 a third slide 70 is arranged which likewise is capable of being moved on the rails 28, 30 in a longitudinal direction indicated by 72 and capable of being fixed at the desired position with the aid of locking screws 74a, 74b. The third slide 70 bears a third clamping element 76 which serves for receiving a material-abrading tool 78. The material-abrading tool 78 has a milling head 80 and is likewise capable of being fastened to the third clamping element 76 in varying angular positions. The third clamping element 76 may, in addition, be moved in a guide groove 82 in a transverse direction indicated by an arrow 84.

In the following, the function of the preparation device 10 will be elucidated in more detail with reference to FIGS. 3 to 10, which show the two vertebrae 16, 18 in an enlarged side view in different subsequent states during the preparation process.

Firstly the patient is aligned and fixed on the operating table 12 in a manner known as such. After the mounting of the reference frame 22 above the patient 20, the surgeon prepares a ventral access canal to the vertebrae 16, 18, which is indicated by 90 in FIG. 2. In principle a dorsal access canal is suitable as well if the patient lies on his/her chest. Spatulas that are required for this purpose may be fastened to the rails 28, 30.

In a next step, the reference frame 22 may be (optionally) tilted about its longitudinal axis, as described above. As a result of such a tilting, a twisting of the vertebral column can be taken into account such as may arise as a result of pathological changes to the bone tissue but also as a result of the exposure of the ventral access canal 90. In order to be able to detect such a twisting, the patient 20 is X-rayed from the side. The operating table 12 is now tilted about its longitudinal axis in such a way that the transverse processes (not shown in FIGS. 1 and 2) of the vertebrae 16, 18 are aligned. Subsequently the reference frame 22 is likewise tilted until no double edges can be detected under fluoroscopy in bores provided in an alignment element 22 which is fastened to the rail 30. In this way, the reference plane defined by the rails 28, 30 extends exactly parallel to the transverse processes of the vertebrae 16, 18. Further particulars relating to this type of alignment are described in an international patent application entitled "System for aligning a material-abrading tool relative to an intervertebral disc compartment", which was filed by the applicant on the same date as the pre-sent application. The full disclosure of this patent application is incorporated herein by reference.

Figure 3:
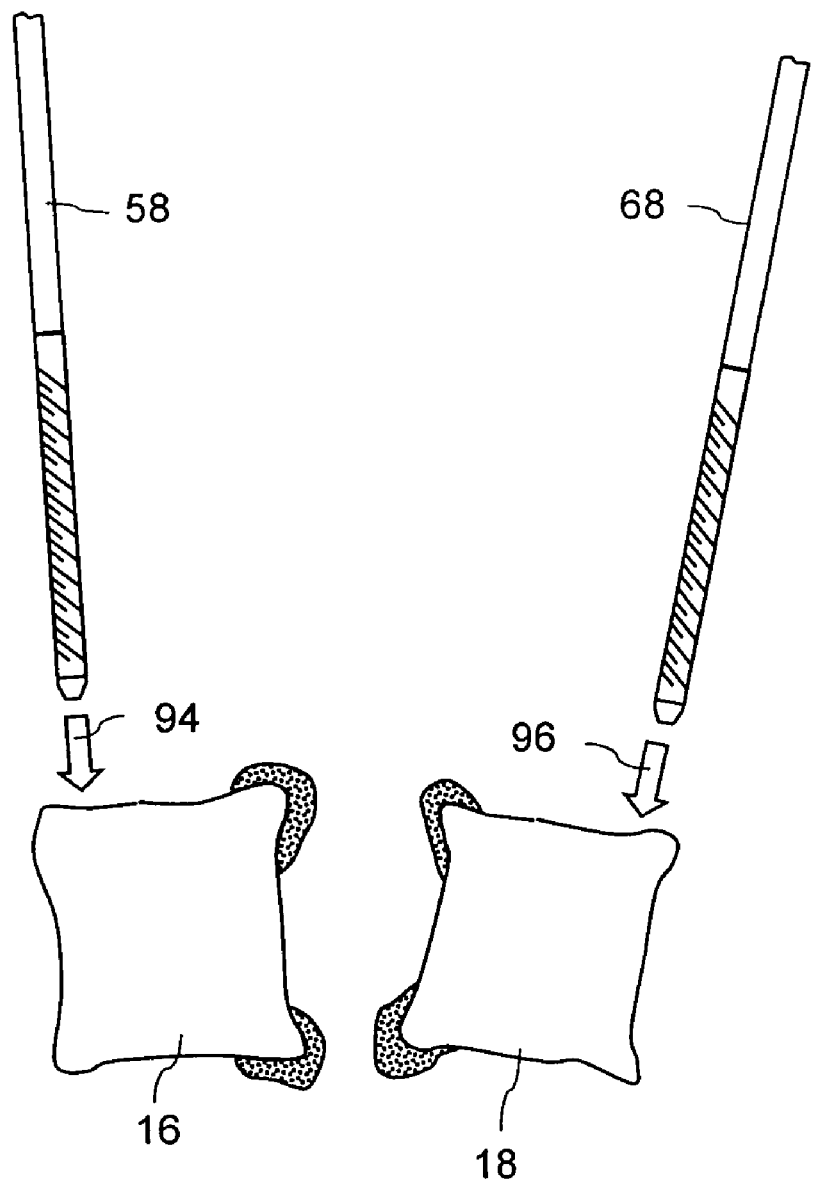
FIGS. 3 to 13 show an intervertebral disc compartment between two adjacent vertebrae in varying states before, during and after the preparation in the case where use is made of the preparation device shown in FIGS. 1 and 2.
Figure 4:
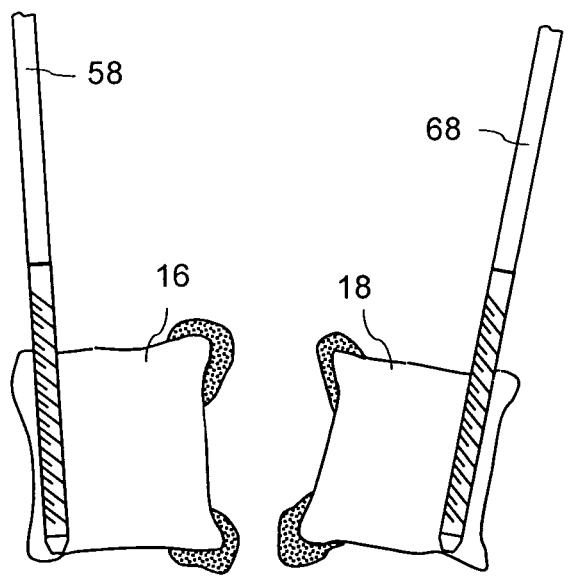

After the (optional) alignment of the reference frame 22 relative to the vertebral column of the patient 20, the fixing screws 58, 68 are, according to a first embodiment, screwed into the vertebrae 16, 18 via the previously exposed ventral access canal 90. The screwing-in operation is indicated in FIG. 3 by arrows 94, 96. In the course of this operation, the fixing screws 58, 68 are screwed in so that they extend—preferably bicortically—through the thick lower plates of the vertebrae 16, 18 which are distal from the intervertebral disc compartment 14, as shown in FIG. 4. In this way, the fixing screws 58, 68 are rigidly connected to the first vertebra 16 and to the second vertebra 18, respectively. Since the thick lower plates are readily detectable radiographically, the precise positioning of the fixing screws 58, 68 relative to the vertebrae 16, 18 is comparatively easy.

In a next step, the two vertebrae 16, 18 are brought into their natural correct anatomical position. This is understood to mean a position that the vertebrae 16, 18 occupy if the patient is in an upright, non-stooped posture and no pathological changes whatsoever—such as, for example, bony processes on the lower plates—have appeared. In case the natural anatomical position of the patient 20 cannot be established on the basis of older radiographs, recourse may also be taken to a biometric survey of the segment of the vertebral column in question. Furthermore, there is the possibility of the surgeon distracting the two fixing screws 58, 68 by hand. In the case of a functioning muscular and ligamentous apparatus, the two vertebrae 16, 18 pass over into their natural anatomical position.

In the course of the transfer of the vertebrae 16, 18 into their natural anatomical position the angle between the two fixing screws 58, 68 will generally have to be changed. The two clamping elements 56, 66, through which the fixing screws 58 and 68 respectively extend, permit such a swivelling of the fixing screws in the forward and rearward directions in a swivel plane that extends perpendicular to the reference plane defined by the rails 28, 30. In the course of this transfer of the vertebrae 16, 18 into their natural anatomical position it will furthermore generally be necessary to move the two slides 50, 60 on the rails 28, 30 while the fixing elements 58, 68 are swivelled in the clamping elements 56 and 66, respectively.

As soon as the natural anatomical position of the vertebrae 16, 18 has been attained, the fixing screws 58, 68 are fixed with the aid of the clamping elements 56, 66 and with the aid of the locking screws 54a, 54b and 64a, 64b, respectively.

Figure 5:
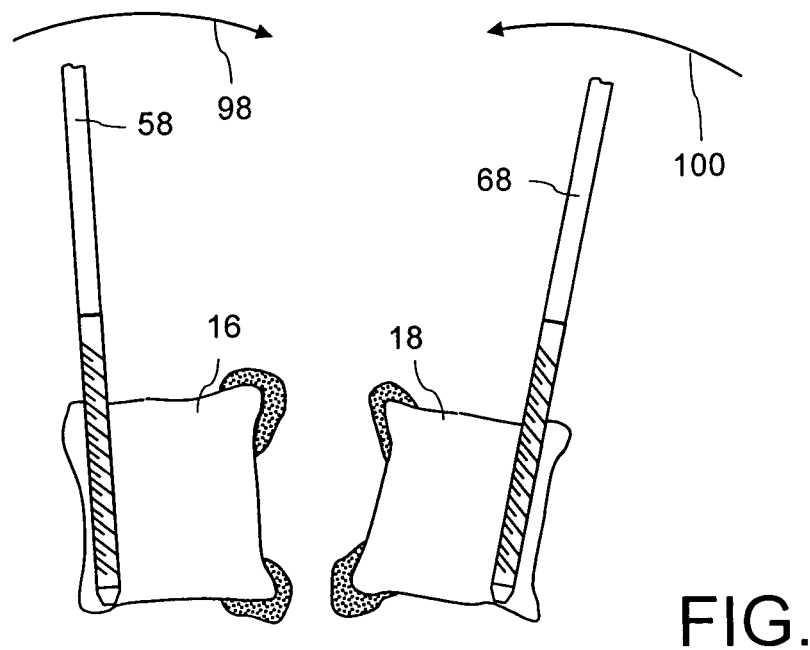

In the embodiment that is represented here, it is assumed that the angle between the two vertebrae 16, 18 has to be made smaller, so that the two fixing screws 58, 68 are swivelled inwards, as indicated in FIG. 5 by arrows 98, 100.

Figure 6:
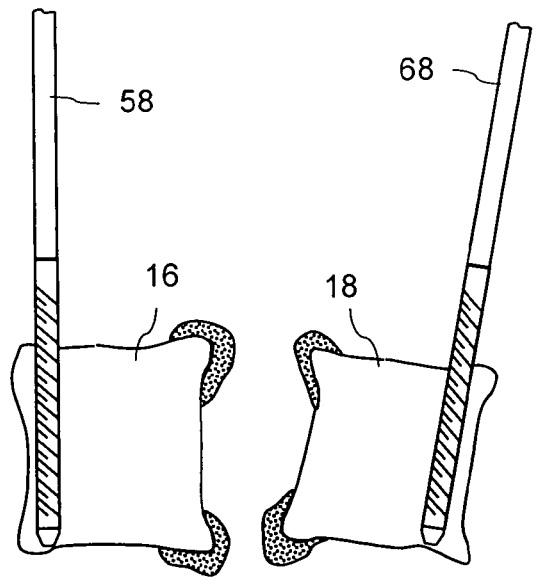

FIG. 6 shows the two vertebrae 16, 18 in their natural anatomical position as established by swivelling the two fixing screws 58, 68 in relation to the stationary reference frame 22.

In this fixed natural anatomical position the adjacent thick plates of the vertebrae 16, 18 pointing towards one another are now machined in material-abrading manner with the aid of the material-abrading tool 78. This is usually necessary in order to remove pathological bone deformations that extend into the spinal canal and often cause severe pain to the patient. As a side effect flat abutment faces for the intervertebral disc prosthesis to be inserted are prepared by this milling operation.

In this embodiment it is assumed that the lower plate of the first vertebra 16 pointing towards the second vertebra 18 is machined first. For this reason, the material-abrading tool 78 is fixed to the third clamping element 76 in such a way that the longitudinal axis of the milling head 80 takes up a predetermined angle relative to the first fixing screw 58. This angle may amount to 2°, for example. In order to set the angle between the material-abrading tool 78 and the first fixing screw 58, a wedge-shaped template 102 can be introduced into the interspace between the first fixing screw 58 and the material-abrading tool 78, as indicated in FIG. 1 by an arrow 104. If another angle between the material-abrading tool 78 and the first fixing screw 58 is to be set, an appropriately shaped different template is to be used.

The spacing between the third slide 70 and the first slide 50 is chosen so that when the material-abrading tool 78 is operated a flat abutment face can be created without an unnecessarily large amount of bone material having to be removed.

Figure 7:
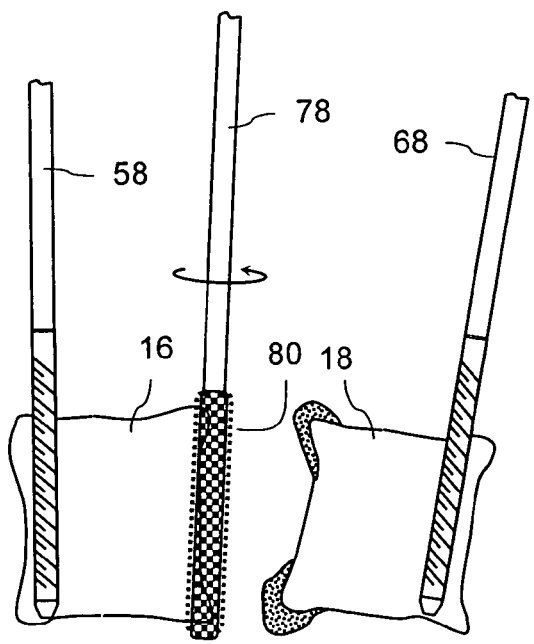

FIG. 7 shows the position of the milling head 80 at the start of the milling operation. The angle and the spacing between the first fixing screw 58 and the milling head 80 is defined with the aid of the clamping elements 56 and 76, respectively, and the slides 50 and 70, respectively, which are fixed to the rails 28, 30. By moving the third clamping element 70 along the guide groove 82, or by means of a swivelling of the milling head 80 in a plane defined by the guide groove 82, a flat abutment face, denoted by 106 in FIG. 8, for a supporting plate of the intervertebral disc prosthesis is now created on the first vertebra 16.

Figure 8:
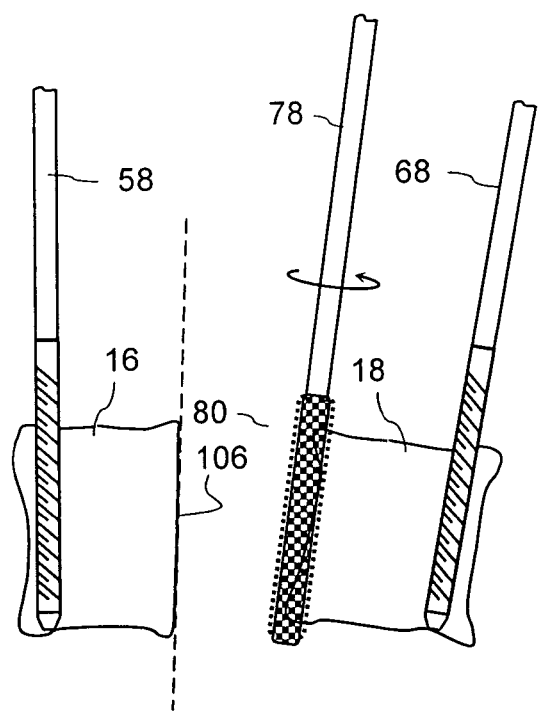

This operation is now repeated in like manner for the second vertebra 18, as indicated in FIG. 8. The abutment face created thereby on the second vertebra 18 is denoted by 108 in FIG. 9.

Figure 9:
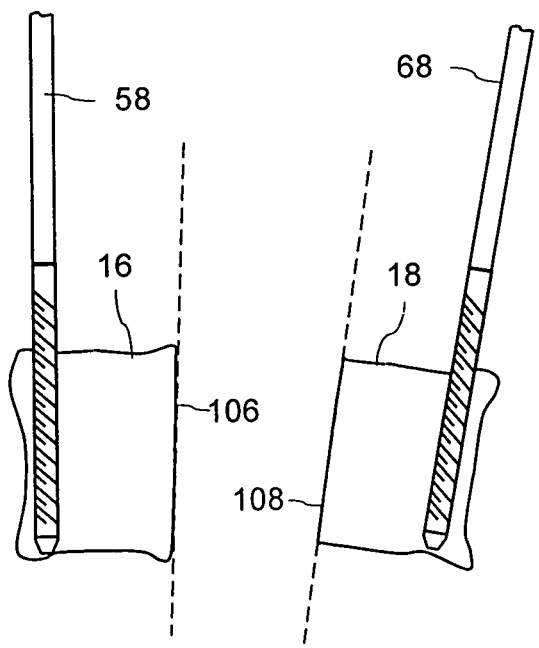

After conclusion of the machining of the vertebrae 16, 18 with the aid of the material-abrading tool 78, the space between the vertebrae 16, 18 is prepared for insertion of the intervertebral disc prosthesis. As FIG. 9 shows, the two abutment faces 106, 108 of the vertebrae 16, 18 facing towards one another are now flat. Given appropriate choice of the template 102, the abutment faces 106, 108 include the natural anatomical angle of the intervertebral disc compartment.

Figure 10:
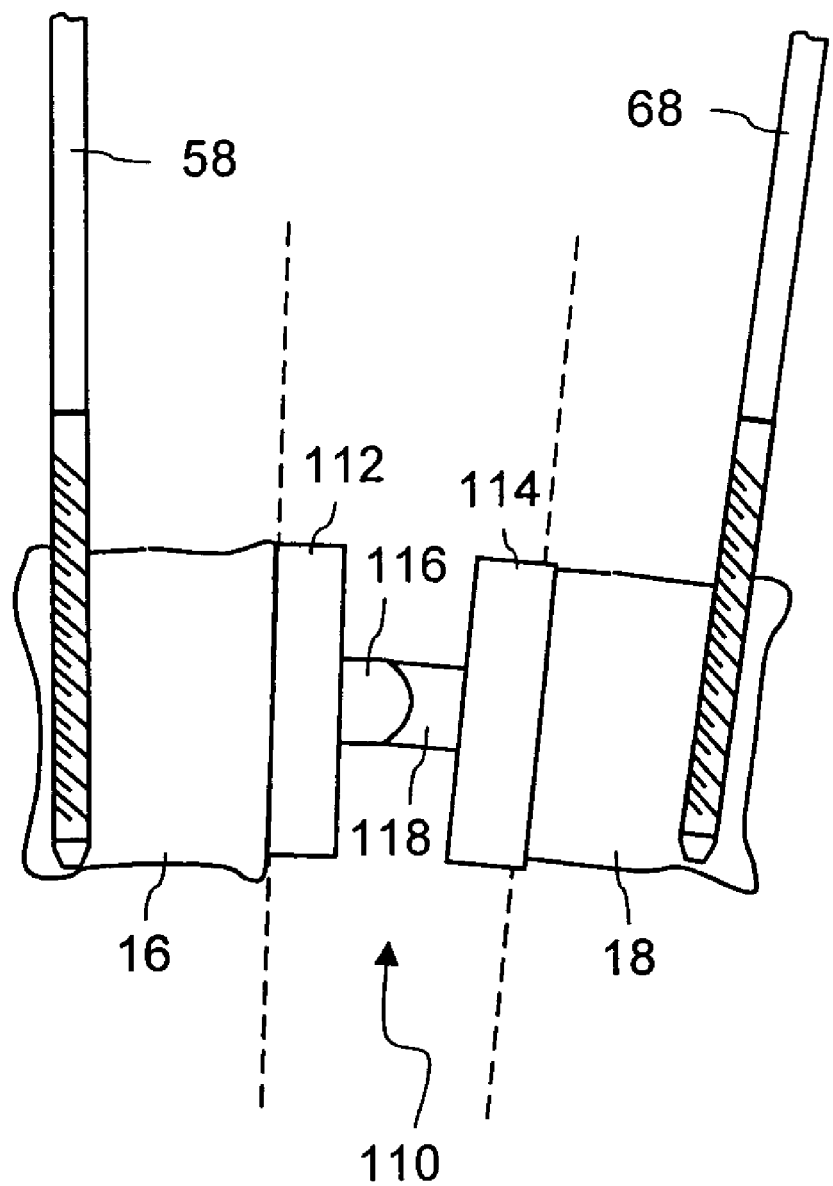

In a next step, an intervertebral disc prosthesis 110 can now be inserted into the prepared interspace between the vertebrae 16, 18 via the previously created ventral access canal, as shown in FIG. 10. The intervertebral disc prosthesis 110 comprises two supporting plates 112, 114 which rest with their outward-pointing sides against the flat-milled faces 106 and 108, respectively, of the vertebrae 16, 18. On the insides the supporting plates 112, 114 bear joint parts 116, 118 which together form a ball-and-socket joint.

It is to be understood that many variations of the method explained above are possible and still within the scope of the invention. For example, according to the method described above, the vertebrae 16, 18 are transferred to their correct anatomical position with the help of the screws 58, 68 prior to the milling operation. This is advantageous if prostheses having a fixed design are used. In this case it is necessary to prepare the intervertebral disc compartment by milling such that the prosthesis is received at its optimum position. The intervertebral disc compartment is thus adapted to the prosthesis.

However, in many cases it is not possible or sensible to adapt the shape of the intervertebral disc compartment to the prosthesis to be inserted. Instead, it is often advantageous to adapt the prosthesis to the intervertebral disc compartment. The latter approach is usually preferable because the surgeon should be as free as possible in his determination which parts of the bone tissue have to be removed. If the surgeon finds during the implant surgery that a substantial part of a vertebra has to be removed as a result of bone degenerations, no care should be taken what implications this will have to the position of the prosthesis.

If the prosthesis is adapted to the intervertebral disc compartment, it is sufficient to transfer the vertebrae to their correct anatomical position after the milling operation. For fixing the vertebrae during the milling operation other conventional means may be used, for example brackets.

Figure 11:
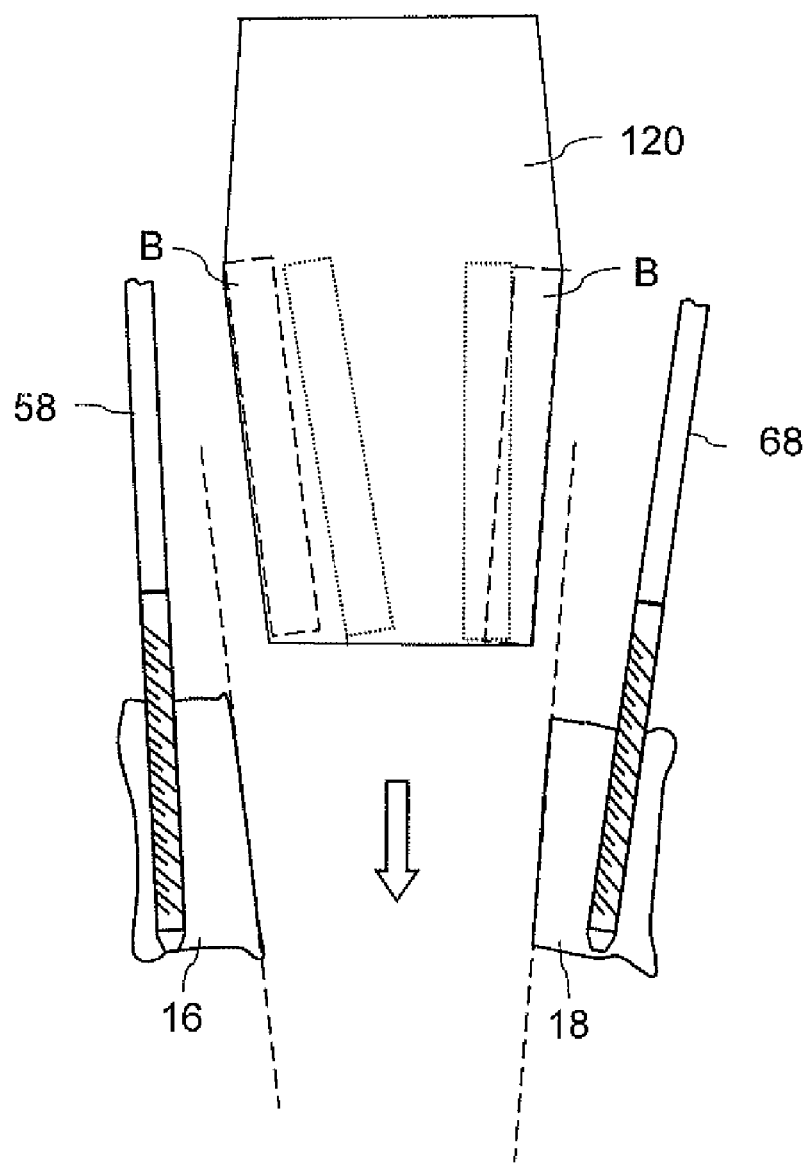
Figure 12:
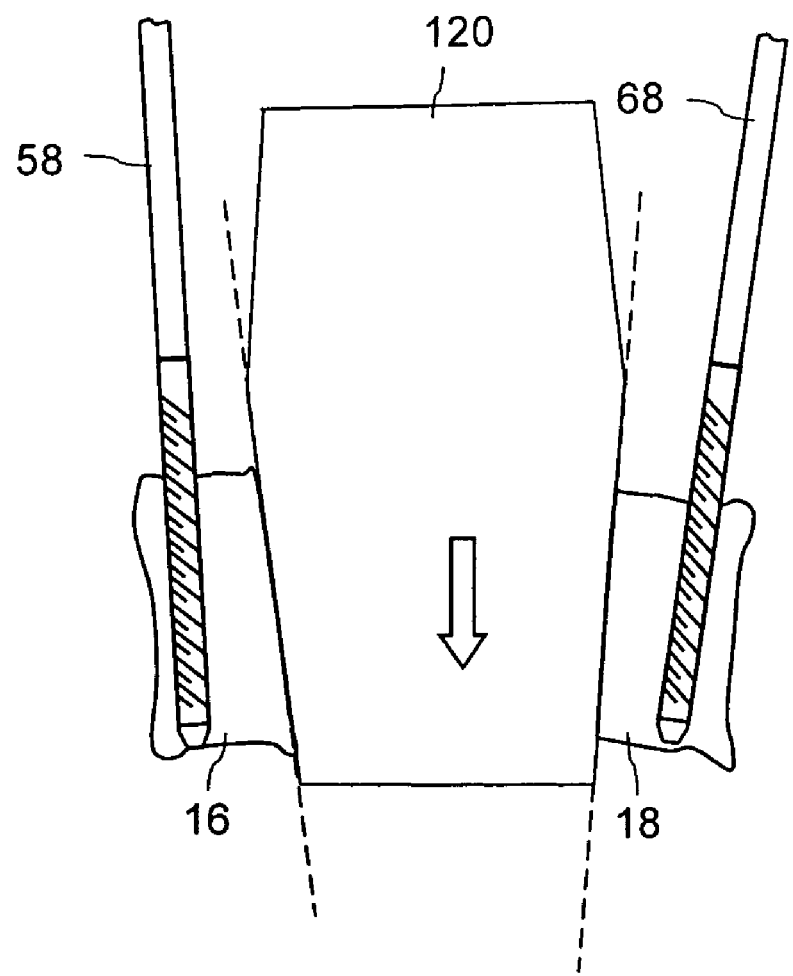

FIG. 11 shows a situation in which a substantial amount of bone material had to be removed by the surgeon using the material-abrading tool 78. After the removal of the bone material the screws 58, 68 are now inserted into the vertebrae 16, 18, and the preparation device 10 is used for transferring the vertebrae 16, 18 into their anatomically correct position that has been determined beforehand on the basis of biometrical data. However, in this position the compartment between the vertebrae 16, 18 has an unknown shape. For determining the shape, a template 120 is inserted (see FIG. 12) into the compartment between the adjacent vertebrae 16, 18 after the adjustment step has been finished. In the embodiment shown it is assumed that the template 120 has adjustable blades (not shown) so that the template 120 can have different geometries. The blades are adjusted until they abut along they edges on the milled surfaces of the vertebrae 16, 18.

Then the template 120 is retracted, and based on the geometry of the compartment determined with the help of the template 120 a prosthesis may now be assembled that perfectly fits into the compartment between the vertebrae 16, 18. A particularly suitable intervertebral disc prosthesis for this purpose is described in the international patent application entitled "Intervertebral disc prosthesis" that has been filed on the same day by the applicant. The full disclosure of this earlier application is incorporated herein by reference. In one embodiment a plurality of different joint parts 116, 118 is provided from which the surgeon selects an appropriate set. This makes it possible to vary the center of curvature of the ball-and-socket joint, and thus to determine the possible movements of the adjacent vertebrae. Ideally the center of curvature of the ball-and-socket joint should be situated as closely as possible to the anatomically predetermined center of motion of the two vertebrae 16, 18. This position can be determined using fluoroscopes or simulation programs. Alternatively, or in addition, supporting plates 112, 114 of varying thickness may be used to position the center of curvature in order.

Figure 13:
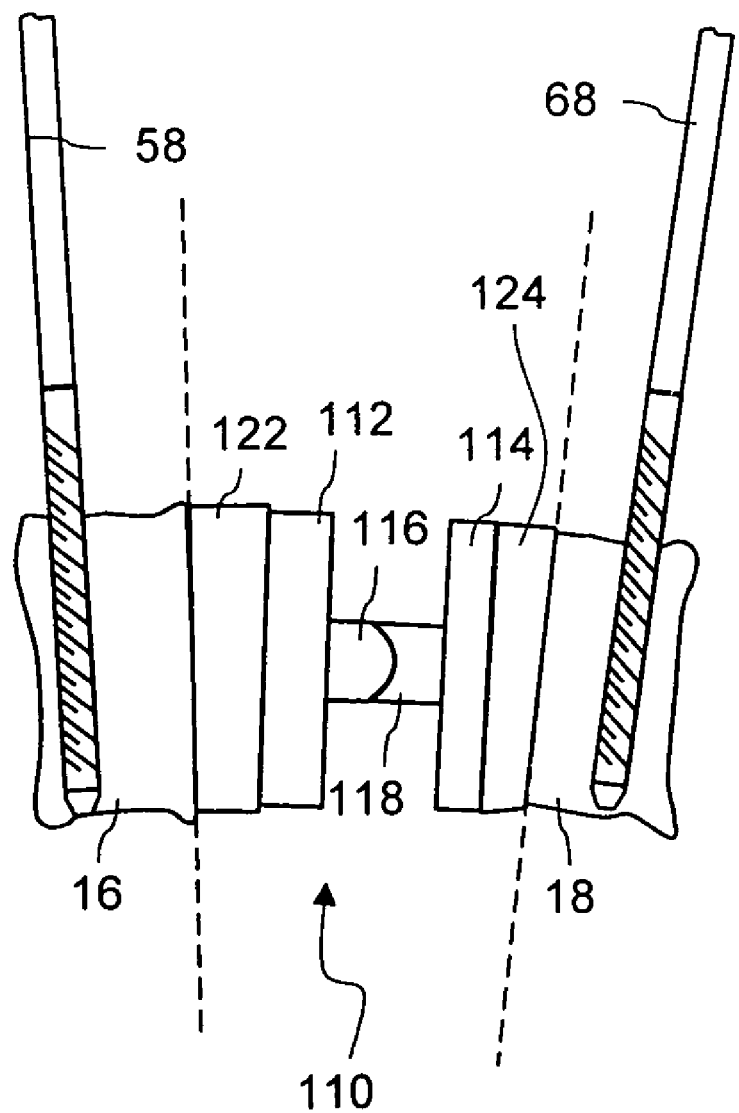

Another alternative for positioning the center of curvature of the ball-and-socket joint as closely as possible to the anatomically predetermined center of motion is the use of additional plates, wedges, or wedged-shaped spacer elements 122, 124 as shown in FIG. 13. Instead (or in addition to) of using supporting plates 112, 114 of varying thickness the spacer elements 122, 124 may be inserted between the outward surfaces of the supporting plates 112, 114 of the intervertebral disc prosthesis 110 and the adjacent vertebrae 16, 18. The spacer elements 122, 124 are selected from a set of spacer elements having two plane surfaces that are parallel to each other (i.e. spacer elements angle equals 0°) or form a spacer element angle between 1° and 45° therebetween. The spacer elements differ from one another with respect to the distance between the plane surfaces and the wedge angle. The suitable spacer elements 122, 124 are selected on the basis of the shape of the compartment measured with the help of the template 120. The intervertebral disc prosthesis 110 is now, together with the spacer elements 122, 124, inserted into the compartment, as has been described above with reference to FIG. 10. In this embodiment, the surgeon may either assemble the intervertebral disc prosthesis 110 immediately prior to its insertion into the intervertebral disc compartment, or even inside the compartment. To this end the surgeon should have direct access to a large variety of differently shaped spacer elements, such as wedge-shaped spacer elements, such that an adjustment to almost any arbitrary shape of the intervertebral disc prosthesis 110 is possible.

The invention claimed is:

1. A method for introducing an intervertebral disc prosthesis into an intervertebral disc compartment formed between a first and a second vertebrae, the method comprising the steps of:
   a) exposing an access canal to the intervertebral disc compartment;
   b) connecting a first fixing element carried by a first slide to the first vertebra;
   c) connecting a second fixing element carried by a second slide to the second vertebra;
   d) adjusting the position of the first and second vertebrae by adjusting the distance between the first and second slides, which adjusts the distance between the first and second fixing elements;
   e) adjusting the angle between the first and second vertebrae by adjusting the angle between the first and second fixing elements independent of adjusting the distance between the first slide and the second slide;
   f) inserting an intervertebral disc prosthesis into the intervertebral disc compartment; and
   g) removing material from at least one vertebra between steps a) and b), between steps d) and f), or both.

2. The method according to claim 1, further comprising determining the geometry of the intervertebral disc compartment between steps d) and f).

3. The method according to claim 2, wherein the step of determining the geometry of the intervertebral disc compartment comprises inserting an adjustable template into the intervertebral disc compartment.

4. The method according to claim 1, further comprising introducing at least one spacer element into the intervertebral disc compartment, said spacer element being positioned between a vertebra and the intervertebral disc prosthesis.

5. The method according to claim 4, wherein the at least one spacer element is wedged-shaped.

6. The method according to claim 4, further comprising selecting the at least one spacer element from a variety of spacers having different geometries.

7. The method according to claim 6, further comprising inserting an adjustable template into the intervertebral disc compartment to determine the geometry of the intervertebral disc compartment, and wherein the step of selecting the at least one spacer element comprises selecting the at least one spacer element on the basis of the geometry of the intervertebral disc compartment determined with the help of the adjustable template.

8. A method according to claim 1, wherein the step of removing comprises:
   connecting a material-abrading tool to a reference frame;
   adjusting an angle between the material-abrading tool and the first or second fixing element; and
   removing material from the first or second vertebra using the material-abrading tool.

9. A method according to claim 1, wherein the step of adjusting the angle between the first and second vertebrae comprises adjusting the angle between the first and second fixing elements until it reaches between 2 and 10 degrees.

10. A method according to claim 1, wherein the step of adjusting the angle between the first and second vertebrae comprises adjusting the angle between the first and second fixing elements until it reaches between 4 and 8 degrees.

11. A method for introducing a supporting plate of an intervertebral disc prosthesis into an intervertebral disc compartment formed between a first and a second vertebrae, the method comprising the steps of:
   (a) exposing an access canal to the intervertebral disc compartment;
   (b) connecting a first fixing element to the first vertebra;
   (c) connecting a second fixing element to the second vertebra;
   (d) adjusting the position of the first and second vertebrae by moving the first and second fixing elements;
   (e) inserting an adjustable template having adjustable blades into the intervertebral disc compartment;
   (f) determining the geometry of the intervertebral disc compartment using the adjustable template;
   (g) removing the adjustable template;
   (h) inserting the intervertebral disc prosthesis into the intervertebral disc compartment; and
   (i) removing material from at least one vertebra between steps (a) and (b), between steps (d) and (i), or both.

12. A method according to claim 11, wherein the step of determining the geometry of the intervertebral disc compartment comprises adjusting the adjustable blades until edges of the blades abut facing surfaces of the first and second vertebra.

13. A method for introducing a supporting plate of an intervertebral disc prosthesis into an intervertebral disc compartment formed between a first and a second vertebrae, the method comprising the steps of:
   (a) exposing an access canal to the intervertebral disc compartment;
   (b) connecting a first fixing element to the first vertebra;
   (c) connecting a second fixing element to the second vertebra;
   (d) inserting an adjustable template into the intervertebral disc compartment to determine the geometry of the intervertebral disc compartment;
   (e) adjusting the position of the first and second vertebrae by moving the first and second fixing elements;
   (f) removing the adjustable template after step (d) or after step (e);
   (g) inserting the intervertebral disc prosthesis into the intervertebral disc compartment;
   (h) positioning at least one spacer element between the intervertebral disc prosthesis and the first or second vertebra, the at least one spacer element being selected from a variety of spacers having different geometries based upon the geometry of the intervertebral disc compartment determined using the adjustable template; and
   (i) removing material from at least one vertebra between steps (a) and (b) or between steps (f) and (g).

14. The method according to claim 13, wherein step (h) is performed after step (g).

15. The method according to claim 13, wherein the step of positioning comprises positioning a spacer element between the intervertebral disc prosthesis and the first vertebra and positioning a spacer element between the intervertebral disc prosthesis and the second vertebra.

16. The method according to claim 13, the step of positioning including that the at least one spacer element is a wedged-shaped spacer element.

* * * * *